United States Patent [19]

Cesti et al.

[11] Patent Number: 4,762,793
[45] Date of Patent: Aug. 9, 1988

[54] PROCESS FOR THE BIOTECHNOLOGICAL PREPARATION OF OPTICALLY ACTIVE ALPHA-ARYLALKANOIC ACIDS

[75] Inventors: Pietro Cesti, Novara; Paolo Piccardi, Milan, both of Italy

[73] Assignee: Montedison S.p.A., Milan, Italy

[21] Appl. No.: 840,856

[22] Filed: Mar. 18, 1986

[30] Foreign Application Priority Data

Mar. 22, 1985 [IT] Italy ................ 20036 A/85

[51] Int. Cl.⁴ ........................... C07P 41/00
[52] U.S. Cl. ..................... 435/280; 435/921
[58] Field of Search ........................ 435/280

[56] References Cited

U.S. PATENT DOCUMENTS 4,565,782  1/1986  Bewick ................ 435/280

*Primary Examiner*—Sam Rosen
*Attorney, Agent, or Firm*—Morgan & Finnegan

[57] ABSTRACT

There is described the preparation of S(+) alpha-arylalkanoic acids by means of the reaction of a racemic ester(R,S) of the formula:

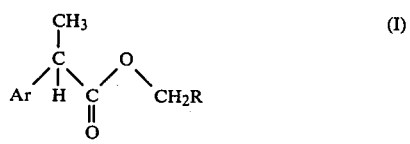

(I)

wherein: R is a group selected from the group consisting of —C≡CH, a —CH=CH$_2$, —CN; —COCH$_3$, —COO alkyl C$_1$C$_4$ and —CH$_2$—O alkyl C$_1$-C4 group, Ar is a group selected from the group consisting of an aryl group and an aryl substituted or condensed with other groups, in particular a group selected from the group consisting of groups of the formula:

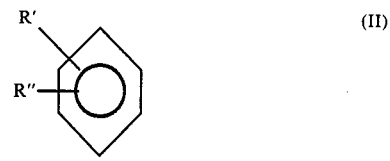

(II)

and

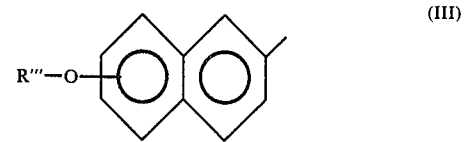 (III)

wherein:

R' is selected from the group consisting of C$_1$-C$_8$ linear or branch of chain alkyl, C$_1$-C$_4$ alkenyl, alkoxy, phenyl, phenoxy, tenoyl and heterocyclic;

R" is selected from the group consisting of hydrogen or halogen;

R''' is a C$_1$-C$_4$ alkyl, with an esterase, produced by microorganisms capable of selectively hydrolizing the S(+) form of said racemic ester and by successively separating the S(+) acid from the unreacted ester.

5 Claims, No Drawings

PROCESS FOR THE BIOTECHNOLOGICAL PREPARATION OF OPTICALLY ACTIVE ALPHA-ARYLALKANOIC ACIDS

BACKGROUND

The present invention concerns a process for biotechnological preparation of arylalkanoic acids resolved in the form of optical S(+) and R(−) isomers.

More particularly, the present invention relates to the biotechnological preparation of α-arylalkanoic acids substantially in the form of an optical S(+) isomer.

Prior to the present invention, as illustrated by the work of T. Y. Shen, Angew Chem, Int. Ed. Engl., 11, 460, 1972 there are known α-arylalkanoic acids and, in particular, α-arylpropionic acids used clinically as non-steroideic anti-inflammatory agents.

The above-mentioned α-arylalkanoic acids having in position α a centre of asymmetry, appear in two optically active S(+) and R(−) enantiomeric forms.

Moreover, it is also known from the Shen publication that the anti-inflammatory activity of one of the enantiomers is greater than the other, as in the case of a number of members of the class of α-methyl-arylacetic acids known by the trade mark: Ibuprofen, Naproxen, Fenoprofen, etc.

Usually, the S(+) enantiomer develops an activity superior to the one of the R(−) enantiomer, as in the case of Ibuprofen (S. S. Adams et al., in Journal Pharm. Pharmacy 28, 256, 1976) or as in the case of Naproxen, in which the activity of the S(+) enantiomer is about 28 times greater than that of the R(−) enantiomer.

It is likewise known to separate the optical isomers of said acids, for example from an article by: D. G. Kaiser et al., in J. Pharm, Science, 2, 269, 1976; and from A. Frank and C. Ruchards in Chemistry Letter, 1431–1434, 1984.

However, the known methods for resolving the two optical isomers have drawbacks from a commercial point of view in that they are complicated, need costly optically active reactants, such as for example the kyral agents like methylbenzylamine, and do not allow, in many cases, the attainment of satisfactory yields.

Thus, there has been a long felt need for the provision of a method that would allow the resolution of the optical isomers of above mentioned acids in a simple and cheap way, and that, also would be efficient and commercially feasible.

OBJECTS OF THE INVENTION

An object of the present invention is to provide a process for the separation of the optical isomers of the α-arylalkanoic acids, in a simple and economical way and industrially advantageous.

A further object of the present invention is to provide a process for obtaining in an efficient manner α-arylalkanoic acids substantially in the form of their S(+) optical isomers.

GENERAL DESCRIPTION OF THE INVENTION

It has now been found that the above referred to and other objects of the invention may be realized by the employment of a biotechnological process of enzymatic asymmetric hydrolysis of the racemic esters of the α-arylalkanoic acids, capable of supplying an acid rich in S(+) form.

More particularly, it has been found that for practically effectuating the desired enzymatic asymmetric hydrolysis suitable enzymes are those produced by a microorganism that is capable of asymmetrically hydrolyzing the racemic ester of the above mentioned acids, that is, capable of selectively hydrolyzing the S(+) enantiomer of the racemic ester, in order to yield an acid substantially in the S(+) form, while leaving the ester in the R(−) form substantially unvaried.

S(+) acid may be easily separated from the R(−) ester by various procedures described herein later in detail.

More particularly, the present invention relates to a process for the biotechnological separation of α-arylalkanoic acids, substantially in the form of an S(+) optical isomer, consisting in reacting a racemic (R,S) ester of an α-arylalkanoic acid of the formula:

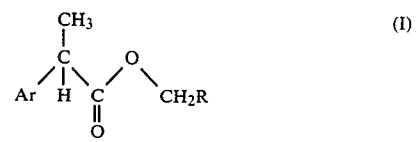

wherein: R is a group selected from the group consisting of —C≡CH, —CH=CH$_2$, —CN, —COCH$_3$—COO alkyl C$_1$–C$_4$ group and a —CH$_2$—O alkyl C$_1$–C$_4$ group. Ar is a group selected from the group consisting of an aryl and an aryl substituted or condensed with other groups, in particular a group selected from the groups consisting of groups of the formula:

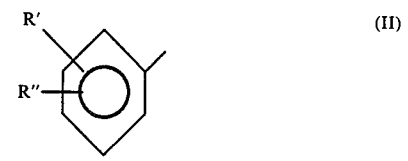

and

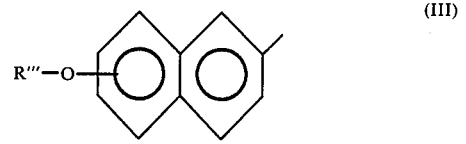

wherein:

R′ is selected from the group consisting of linear and branched alkyl containing from 1 to 8 carbon atoms, alkenyl containing from 1 to 4 carbon atoms, alkoxy, phenyl, phenoxy, tenoyl and heterocyclic;

R″ is selected from the group consisting of hydrogen and halogen;

R‴ is an alkyl containing from 1 to 4 carbon atoms; with an esterase, produced by microorganisms capable of asymmetrically hydrolizing, in a predominant way, the S(+) form of the racemic ester of formula (I), and by then separating with known techniques the acid obtained substantially in the S(+) form from the unreacted ester, substantially in the R(−) form.

The racemic esters of formula (I) may be prepared according to the conventional esterification processes, for instance according to the following reactions:

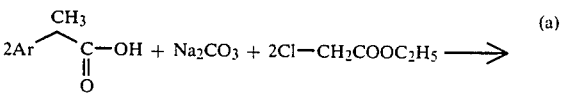

-continued

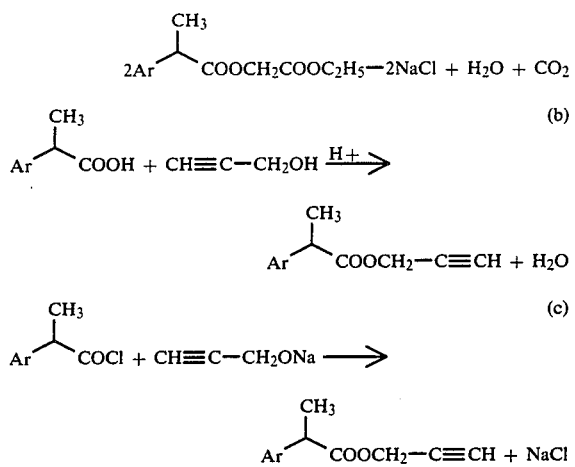

The esterase which may be used according to the process of the present invention is a lipase soluble in water and is produced by microorganisms.

Particularly suited for the purpose of this invention proved to be the lipase produced by the microorganism 'CANDIDA CYLINDRACEA' filed under no. 14830 with the "American Type Culture Collection, USA (ATCC).

The aforementioned lipase is convenient to use since the microorganism which produces such a lipase may be grown on a liquid nutritional soil according to conventional procedures, for example by inoculating the microorganism into a sterilized liquid culture ground and made to grow on an alternating shaker at between 20° C. and 40° C. for a period of 1 to 3 days.

The asymmetric hydrolysis reaction of the racemic esters of formula (I) is carried out by vigorously stirring the mixture of racemic ester with raw or purified esterase which may be contained in a liquid like water or in the same culture broth of the microorganism, or its extracts or concentrates, or with the suspensions of the microorganism cells.

Alternatively, the enzyme may be used tied up on a substrate of various nature, chosen according to the techniques of the Prior Art in that specific field.

The process according to the present invention may be conducted at temperatures in the range between 10° and 60° C., but preferably in the range between 20° C. and 40° C., while maintaining the pH value of the reaction mixture in the range between 5 and 9, but preferably between 6 and 8, at which pH the enzymes seems to develop the greatest activity.

The pH of the reaction medium is maintained constant by the use of a buffer solution or by means of the neutralization of the acidity that is formed with a base such, as for instance, KOH, NaOH, etc.

The concentration of the starting racemic ester in the reaction mixture may vary from 1% to 20% by weight.

The duration of the asymmetric hydrolysis reaction may vary from 5 to 64 hours, depending on the specific activity of the enzyme used, which in general depends on its degree of purity.

At the end of the asymmetric hydrolysis reaction, from the reaction mixture there may be extracted the acid that has richly formed in the S(+) isomer and the ester not reacted rich in the R(−) isomer, by using water-immiscible organic solvents such as, for example, methylene chloride; toluene; lygroine ethyl ether and the like.

From the organic extract thus obtained and successively concentrated, there may then be separated the acid, substantially in the S(+) form, from the ester which substantially is in the R(−) form, by passing the extract through a chromatographic column, using as a stationary phase, for instance, a silica gel.

Alternatively, one may isolate the rich acid in the S(+) eniantomer extracting it from the reaction mixture by means of basic washups, using for the purpose such for example aqueous solutions of NaOH at 5% concentration or KOH at a 10% concentration.

The non-hydrolyzed ester and rich in the R(−) form, separated as indicated above, may then be subjected to a racemization by treating it with bases in a anhydrous medium and successively re-utilized as starting material in the process of this invention, that is, it may be subjected anew to an enzymatic asymmetric hydrolysis.

In a more complicated and, in general, less convenient way, said R(−) ester may be hydrolized to R(−) acid which, after a suitable racemization and subsequent re-esterification, will provide an (S,R) racemic ester which may be recycled for use into the process of the invention.

In the following are given a few examples for further purely illustrative purposes, without any limiting intentions involving the inventive idea of this invention.

SPECIFIC DESCRIPTION OF THE INVENTION

EXAMPLE 1

Preparation of S(+) 2-(4-isobutylphenyl)propionic acid

To 100 ml of a buffer solution of 0.2M of $NaHPO_4$ and $KH_2PO_4$ at a pH of 7, there were added 2.92 g of etoxycarbomethyl ester of the (R,S) 2-(4-isobutylphenyl)propionic acid, 400 mg of the lipase enzyme from "CANDIDA CYLINDRACEA" (marketed by SIGMA Chemical CO. USA, with 30% of proteins, and displaying an activity of 1400–2800 units per mg of proteine).

The mixture was vigorously stirred for 24 hours, at a temperature of 28° C. The mixture was then extracted with methylene chloride. This extract was analyzed for HPLC (Erbasil RP-18, $CH_3CN/H_2O$ 75/25, 254 nm, UV-detection) and the conversion was calculated on the basis of the relationships or ratios between the peaks of the acid that has formed and those of the unreacted ester. The HPLC analyses have proved a conversion of 45%, equal to 90% of hydrolysis of the S(+) form. The extract was concentrated and subjected to chromatography on column, using as a stationary phase a silica gel and as an eluent a hexane ether mixture in the ratio of 3:1.

The structure of the acid was confirmed by the NMR analysis.

The solid product thus obtained has proved to have a melting point equal to 49° C. and a rotatory power $[\alpha]_D^{20} = +55.55°$ (C=1, $C_2H_5OH$).

The GLC analyses, as S(−)α-methylbenzamide derivative, have shown an optical purity $\geq 95\%$.

EXAMPLE 2

To 100 ml of a 0.1M KCl solution were added 2.4 g of propargyl ester of the (R,S) 2-(4-isobutylphenyl)propionic acid, and 400 mg of the lipase enzyme from CANDIDA CYLINDRACEA of example 1.

The mixture was vigorously stirred maintaining the pH on a constant value of 6.8 with the addition of an aqueous solution of 0.5M KOH at a temperature of 37° C.

After 48 hours, on the basis of the quantity of consumed KOH, it was found that the conversion to 2-(4-isobutylphenyl)propionic S(+) acid amounted to about 40%.

The successive separations and analyses were conducted in accordance with the procedures indicated in Example 1. The solid product showed a: $[\alpha]_D^{20} = +54.9°$ (C=1, C$_2$H$_5$OH) and a melting point of 49° C.

EXAMPLE 3

Into a flask of 500 cc holding capacity were placed 100 cc of culture soil prepared by dissolving 10 g of glucose, 5 grams of peptone, 3 g of malt extract and 2 g of yeast extract in 1 lt of H$_2$O, and the pH was then brought up to 6.5.

After sterilization, the culture soil was inoculated with a SLANT of CANDIDA CYLINDRACEA A.T.C.C. no. 14830 microorganism and was then put to incubate for 52 hours at 30° C. in a rotary shaker revolving at 350 rpm.

The pH of the reaction medium was then adjusted to value 7, using for the purpose an aqueous solution 0.5M of KOH, to which were then added 2.92 g of ethoxycarbomethyl ester of the (R,S) 2-(4-isobutylphenyl)propionic acid. This mixture was thereupon subjected to stirring for 48 hours at a temperature of 30° C., while the pH was kept constant by the slow addition of an aqueous solution of 0.5M KOH.

The successive separations and analyses were conducted in accordance with the procedures indicated in example 1.

The S(+)2-(4-isobutylphenyl)propionic acid, obtained with a conversion of 38%, has proved that: $[\alpha]_D^{20} = +53.2°$ (C=1, C$_2$H$_5$OH) while the melting point amounted to 48° C.

EXAMPLE 4

Preparation of 2-(6-methoxy-2-naphtyl)propionic acid

To 100 ml of a 0.3M buffer solution of phosphate (NaHPO$_4$+KH$_2$PO$_4$) were added 3.2 g of cyanomethyl ester of 2-(6-metoxy-2-naphtyl)propionic acid, and 500 mg of CANDIDA CYLINDRACEA enzyme of example 1. This mixture was then stirred vigorously for 52 hours at a temperature of 32° C. The analyses showed a conversion of the (R,S) Racemic ester to the corresponding S(+) acid amounting to 40%.

The separations and analyses were conducted in accordance with the procedures followed in example 1.

The product thus obtained was crystallized from an acetone/hexane mixture and was fund to have the following characteristics:

Melting point (m.p.)=154° C.; $[\alpha]_D^{20} = +65.14°$ (C=1; CHCl$_3$).

EXAMPLES FROM 5 TO 10

Operating according to the procedures described in example 1 by using buffer solutions of NaHPO$_4$ and KH$_2$PO$_4$ with a pH=6.5, a temperature of 32° C. and the reactants reported on the table I, there were obtained the conversions to the corresponding S(+) acids as reported on table 1, said conversions being calculated either with respect the the starting (R,S) racemic ester or with respect to the S(t)ester. The optical purities of the obtained acids always proved greater than 90%.

TABLE 1

| Ex. | Ar (Racemic ester (R,S) Ar—CH(CH$_3$)—COOCH$_2$R) | R | Racemic ester (R,S) g. | Lipase enzyme from Candida Cylindracea g. | Buffer (NaHPO$_4$ + KH$_2$PO$_4$) ml | Reaction time hrs. | Conversion racemic ester % | Conversion S(+) ester % |
|---|---|---|---|---|---|---|---|---|
| 5 | 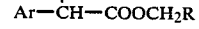 | —CH=CH$_2$ | 2 | 0.3 | 50 | 45 | 48 | 96 |
| 6 |  | —C(=O)—CH$_3$ | 3 | 0.2 | 100 | 30 | 35 | 68 |
| 7 |  | —CN | 3 | 0.4 | 70 | 42 | 40 | 76 |
| 8 |  | —COOCH$_3$ | 4 | 0.4 | 100 | 28 | 30 | 59 |
| 9 |  | —CN | 2 | 0.2 | 50 | 24 | 47 | 92 |

TABLE 1-continued

| Ex. | Ar | Racemic ester (R,S) $Ar-\overset{CH_3}{\underset{|}{CH}}-COOCH_2R$ R | Racemic ester (R, S) g. | Lipase enzyme from *Candida Cylindracea* g. | Buffer (NaHPO$_4$ + KH$_2$PO$_4$) ml | Reaction time hrs. | Conversion racemic ester % | Conversion S(+) ester % |
|---|---|---|---|---|---|---|---|---|
| 10 | 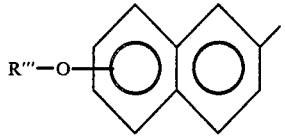 | —CH$_2$—OC$_2$H$_5$ | 3 | 0.5 | 70 | 32 | 32 | 60 |

What we claim is:

1. Process for the biotechnological preparation of α-arylalkanoic acids, substantially in the form of an optical S(+)isomer, said process consisting in reacting a racemic (R,S) ester of an α-arylalkanoic acid of the formula:

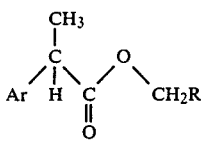 (I)

wherein: R is a group selected from the group consisting of —C≡CH, —CH=CH$_2$, —CN, —COCH$_3$, —COO alkyl C1-C4 and a —CH$_2$—O-alkyl C$_1$-C$_4$ group, Ar represents a group selected from the group consisting of those having the formula:

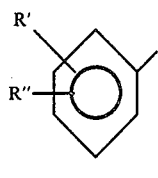 (II)

and $$R'''-O-\text{(naphthyl)}$$ (III)

wherein: R' is a group selected from the group consisting of linear and branched alkyl containing from 1 to 8 carbon atoms, alkenyl containing from 1 to 4 carbon atoms, alkoxy, phenyl, phenoxy, tenoyl and heterocyclic; R" is selected from the group consisting of hydrogen and halogen; R''' is an alkyl containing from 1 to 4 carbon atoms; with CANDIDA CYLINDRACEA lipase produced by microorganisms capable of asymmetrically hydrolyzing, in a predominant way, the S(+) form of the racemic ester of formula (I) and then separating the acid obtained, substantially in the S(+) form, from the unreacted ester, substantially in the R(−) form.

2. Process according to claim 1, characterized in that the esterase is contained in the cells of the microorganisms or in a culture liquid, in extracts or concentrates of said microorganisms.

3. Process according to claim 1, characterized in that the asymmetric hydrolysis reaction is conducted at a pH in the range between 5 and 9.

4. Process according to claim 1, characterized in that the reaction temperature is in the range between 20° C. and 40° C.

5. Process according to claim 1, characterized in that the concentration of the racemic ester of formula (I) in the reaction mixture is in the range between 1% by weight and 20% by weight.

* * * * *

UNITED STATES PATENT AND TRADEMARK OFFICE
CERTIFICATE OF CORRECTION

PATENT NO. : 4,762,793

DATED : August 9, 1988

INVENTOR(S) : Pietro Cesti and Paolo Piccardi

It is certified that error appears in the above-identified patent and that said Letters Patent is hereby corrected as shown below:

IN THE SPECIFICATION:

Table 1, Example 6, the double bond has been omitted and should read as follows:

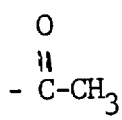

UNITED STATES PATENT AND TRADEMARK OFFICE
CERTIFICATE OF CORRECTION

PATENT NO. : 4,762,793

DATED : August 9, 1988

INVENTOR(S) : Pietro Cesti and Paolo Piccardi

It is certified that error appears in the above-identified patent and that said Letters Patent is hereby corrected as shown below:

In Example 10, the aromatic bonds in the ring have been omitted and should read as follows:

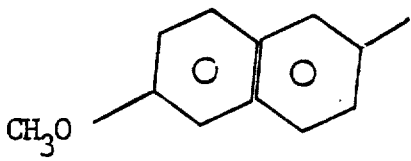

Signed and Sealed this

Eighteenth Day of April, 1989

*Attest:*

DONALD J. QUIGG

*Attesting Officer*   *Commissioner of Patents and Trademarks*